(12) United States Patent
Windecker et al.

(10) Patent No.: US 8,461,356 B2
(45) Date of Patent: Jun. 11, 2013

(54) PROCESS FOR OBTAINING MALEIC ANHYDRIDE BY DISTILLATION

(75) Inventors: Gunther Windecker, Ludwigshafen (DE); Gerd Kaibel, Lampertheim (DE); Michael Steiniger, Neustadt (DE); Thilo Buntrock, Mutterstadt (DE); Jens Weiguny, Freinsheim (DE); Dany Vanden Hautte, Bernissart (BE); Thierry Lurquin, Feluy (BE)

(73) Assignee: BASF SE (DE)

( * ) Notice: Subject to any disclaimer, the term of this patent is extended or adjusted under 35 U.S.C. 154(b) by 724 days.

(21) Appl. No.: 12/532,660

(22) PCT Filed: Mar. 19, 2008

(86) PCT No.: PCT/EP2008/053322
§ 371 (c)(1),
(2), (4) Date: Sep. 23, 2009

(87) PCT Pub. No.: WO2008/116810
PCT Pub. Date: Oct. 2, 2008

(65) Prior Publication Data
US 2010/0113805 A1      May 6, 2010

(30) Foreign Application Priority Data

Mar. 23, 2007  (EP) .................................. 07104826

(51) Int. Cl.
*C07D 307/36* (2006.01)
(52) U.S. Cl.
USPC ....................................................... 549/262
(58) Field of Classification Search
USPC ......................................................... 549/262
See application file for complete search history.

(56) References Cited

U.S. PATENT DOCUMENTS

| 2,271,134 | A |  | 1/1942 | Will et al. |
| 4,118,403 | A | * | 10/1978 | White ........................... 549/262 |
| 4,230,533 | A |  | 10/1980 | Giroux |
| 5,585,502 | A | * | 12/1996 | Ruggieri et al. .............. 549/262 |
| 6,090,245 | A | * | 7/2000 | Brown et al. ................... 203/49 |
| 6,921,830 | B2 | * | 7/2005 | Rahn et al. ..................... 549/262 |

FOREIGN PATENT DOCUMENTS

| DE | 2261044 | 6/1973 |
| EP | 122 367 | 10/1984 |
| EP | 126 288 | 11/1984 |
| EP | 133 510 | 2/1985 |

(Continued)

*Primary Examiner* — Taylor Victor Oh
(74) *Attorney, Agent, or Firm* — Novak Druce Connolly Bove + Quigg LLP

(57) ABSTRACT

What is described is a process for obtaining maleic anhydride by distillation from a solution of maleic anhydride in a high-boiling absorbent which has been obtained by gas phase oxidation of a hydrocarbon and at least partial absorption of the oxidation products into the absorbent, by
i) introducing the solution into the side of a feed column with a rectifying section disposed above the feed point and a stripping section disposed below the feed point,
ii) providing an upper combining column which communicates with the upper end of the rectifying section and a lower combining column which communicates with the lower end of the stripping section,
iii) providing a draw column which communicates with the upper combining column and the lower combining column,
iv) drawing maleic anhydride off as a side draw from the draw column, and drawing off compounds having a lower boiling point than maleic anhydride at the top of the upper combining column and the high-boiling absorbent at the bottom of the lower combining column.
The maleic anhydride obtained as a side draw has a low content of acrylic acid and acetic acid.

18 Claims, 1 Drawing Sheet

FOREIGN PATENT DOCUMENTS

| | | |
|---|---|---|
| EP | 0612714 | 8/1994 |
| EP | 640 367 | 3/1995 |
| EP | 0928782 | 7/1999 |
| WO | WO-96/29323 | 9/1996 |
| WO | WO-03/078057 | 9/2003 |
| WO | WO-03/078058 | 9/2003 |
| WO | WO-03/078059 | 9/2003 |
| WO | WO-03/078310 | 9/2003 |

* cited by examiner

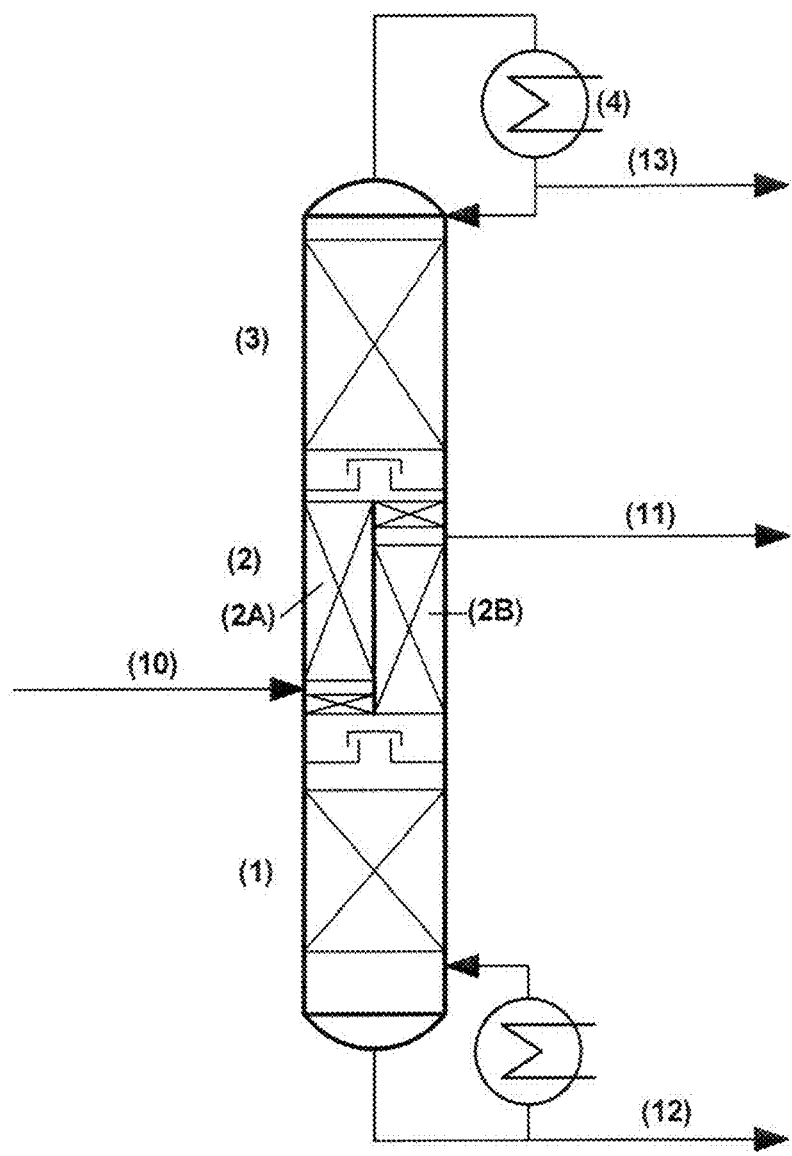

PROCESS FOR OBTAINING MALEIC ANHYDRIDE BY DISTILLATION

CROSS REFERENCE TO RELATED APPLICATIONS

This application is a national phase of PCT/EP2008/053322, filed on Mar. 19, 2008 which claims priority to EP 07104826.8 filed Mar. 23, 2007, the entire contents of all are hereby incorporated by reference.

The invention relates to a process for obtaining maleic anhydride by distillation from a solution of maleic anhydride in a high-boiling solvent which has been obtained by gas phase oxidation of a hydrocarbon and at least partial absorption of the oxidation products into the absorbent.

Maleic anhydride (MA) is prepared on the industrial scale by catalytic gas phase oxidation of hydrocarbons, such as benzene, n-butenes or n-butane. Usually, heterogeneous catalysts based on vanadyl pyrophosphate $(VO)_2P_2O_7$ (so-called VPO catalysts) are used. As well as maleic anhydride, the resulting gaseous reaction mixture comprises in particular water, carbon monoxide and carbon dioxide. Small amounts of acetic acid and acrylic acid are also formed. The reaction products may comprise phosphorus compounds to a small extent, for example triethyl phosphate or phosphoric acid, which are metered into the reaction gas to prolong the catalyst lifetime and increase conversion and/or selectivity, or oxidation products thereof.

The gas mixture leaving the reactor is cooled and sent to further workup. In order to remove the MA formed from the gas stream, it is appropriately contacted with a high-boiling absorbent, for example dibutyl phthalate or diisobutyl hexahydrophthalate, which dissolves the MA in the absorbent. The crude solution thus obtained is sent to a usually multistage distillative workup in order to obtain the MA in the necessary purity. The workup can in principle be effected either continuously or batchwise.

For example, EP-A 0928782 describes a process for the batchwise workup of MA. First, crude MA is isolated from the absorbent solution in a stripping column. The crude MA is then freed of the low boilers in a batchwise column. Medium boilers are drawn off as vapor via the top and passed at least partly back into the column as condensate. Pure MA is drawn off at a point below the top draw. The publication also makes reference to the fact that this type of workup can also be performed continuously. To this end, low boilers should first be removed from the crude MA via the top in a first column. In a second column, the high boilers are removed and the pure MA is obtained.

WO 96/29323 relates to a process for depleting fouling components from the absorbent circuit. It is stated that a liquid side draw of crude MA is drawn off continuously in a first column. The crude product is then fed to at least one further purification stage (which is not shown or described).

EP-A 0612714 describes obtaining pure MA via a three-stage distillation. In a first column, crude MA is obtained via the top, while the absorbent is conducted back to the absorption stage in circulation via the bottom. The crude MA is then separated from the low boilers in the second column and subsequently from the relatively high-boiling components in the third column, which can be recycled back into the first column if required. The pure MA is obtained as a top stream of the third column. The acrylic acid content is said to be less than 100 ppm and the maleic acid content as the free acid less than 500 ppm.

SUMMARY OF THE INVENTION

It is an object of the invention to specify a process with which MA is obtained with comparable purity, preferably MA of improved purity, with a significantly lower level of apparatus complexity.

The object is achieved by a process for obtaining maleic anhydride by distillation from a solution of maleic anhydride in a high-boiling absorbent which has been obtained by gas phase oxidation of a hydrocarbon and at least partial absorption of the oxidation products into the absorbent, by i) introducing the solution into the side of a feed column with a rectifying section disposed above the feed point and a stripping section disposed below the feed point, ii) providing an upper combining column which communicates with the upper end of the rectifying section and a lower combining column which communicates with the lower end of the stripping section, iii) providing a draw column which communicates with the upper combining column and the lower combining column, iv) drawing maleic anhydride off as a side draw from the draw column, and drawing off compounds having a lower boiling point than maleic anhydride at the top of the upper combining column and the high-boiling absorbent at the bottom of the lower combining column.

The maleic anhydride can be withdrawn in liquid or gaseous form at the side draw, preferably in liquid form. The maleic anhydride obtained as the side draw generally has a purity of at least 99% by weight, preferably at least 99.5% by weight. The process according to the invention permits maleic anhydride to be obtained with a content (w/w) of less than 10 ppm, usually less than 5 ppm, of acrylic acid and/or less than 10 ppm, usually less than 5 ppm, of acetic acid by simple distillation. It is assumed that high contents of acids, especially unsaturated acids, such as acrylic acid or oligomers thereof, and/or acetic acid lead to discoloration of the maleic anhydride and products produced therefrom (lack of color number stability).

The compounds having a lower boiling point than maleic anhydride can in principle be drawn off in gaseous or liquid form at the top of the upper combining column. Appropriately, the vapors drawn off at the top of the upper combining column are condensed at least partly, and the condensate is recycled completely or at least partly into the upper combining column. Compounds having a lower boiling point than maleic anhydride can be removed either as vapors or via a substream of the condensate. The condensation temperature is preferably from 55 to 80° C., more preferably from 58 to 70° C.

The bottom of the lower combining column is heated with at least one installed and/or external heater. The external heater can work with forced or natural circulation. The holdup of the bottom and of the accompanying heater should be selected at a minimum level in order to substantially prevent thermal decomposition of the absorbent and/or formation of fouling components (for example fumaric acid). One example of a possibility for this purpose is a design with a divided column bottom.

The high-boiling absorbent drawn off at the bottom of the lower combining column can be recycled into the absorber (described below), in which the oxidation products of the gas phase oxidation are absorbed at least partly into the absorbent.

The feed column, draw column, upper combining column and lower combining column may be discreet components or be designed as a section or chamber of a column which combines several functions. The expression "communicating columns" means that there is exchange both of ascending vapors and of descending condensate between them. Between the feed column and/or draw column and the upper combining column, a condenser for the vapors ascending out of the feed column or draw column can be provided. Between the feed column and/or draw column and the lower combining column, a heater for the condensate effluxing from the feed column or draw column may be provided. However, preference is given to using no such intermediate heaters or condensers.

In a preferred embodiment, a so-called dividing wall column is used for the distillation, i.e. the feed column and the draw column are designed as subchambers open at both sides to a combining chamber on each side, which extend over a section of the longitudinal dimension of a column and are divided by a dividing wall. Distillation columns which comprise a dividing wall are known per se and are described, for example, in U.S. Pat. Nos. 2,271,134, 4,230,533, EP-A 122 367, EP-A 126 288, EP-A 133 510, Chem. Eng. Technol. 10 (1987) 92-98; Chem,-Ing.-Techn. 61 (1989) No. 1, 16-25; Gas Separation and Purification 4 (1990) 109-114; Process Engineering 2 (1993) 33-34; Trans IChemE (1994) Part A 639-644 and Chemical Engineering 7 (1997) 72-76. The dividing wall may be installed into the column in a fixed manner, for example welded in, or else it is secured in the column so as to be removable, for example inserted. The removable securing offers advantages, such as greater flexibility, simpler packing of the column with internals and lower capital costs.

In alternative embodiments, thermally coupled columns are used for the distillation, for example a distillation column with a thermally coupled precolumn, i.e. the draw column, the upper combining column and the lower combining column are designed as a one-piece distillation column and the feed column is designed as a precolumn to the distillation column. Alternatively, it is also possible to use a distillation column with a thermally coupled postcolumn, i.e. the feed column, the upper combining column and the lower combining column are designed as a one-piece distillation column and the draw column is designed as a postcolumn to the distillation column. Distillation columns with connected auxiliary columns are known per se and are familiar to those skilled in the art.

The feed column, the upper combining column, the lower combining column and the draw column comprise separating internals, such as separating trays, for example perforated trays or valve trays, structured packings, for example sheet metal or fabric packings such as Sulzer Mellapak, Sulzer BX, Montz B1 or Montz A3 or Kühni Rhombopak, or beds of random packings, for example Dixon rings, Raschig rings, high-flow rings or Raschig super rings. It is preferred that at least the feed column and/or draw column are provided in their entirety or in some regions with structured packings. Particularly useful packings have been found to be structured packings, preferably sheet metal or fabric packings, of a specific surface area of from 100 to 750 $m^2/m^3$, especially from 250 to 500 $m^2/m^3$. They permit high separating performances at low pressure drops.

When a dividing wall column is used, especially a column with random packings or column with structured packings, the dividing wall can be designed with heat insulation at least in some regions, for example have a double-wall design with intermediate gas space or an internal thermally insulating layer. A description of the various means of thermally insulating the dividing wall can be found in EP-A 640 367.

The total number of theoretical plates of upper combining column, feed column, draw column and lower combining column is preferably from 15 to 80, especially from 20 to 60.

The upper combining column and the lower combining column preferably each independently account for from 1 to 60%, especially from 1 to 30%, of the total number of theoretical plates of upper combining column, feed column, draw column and lower combining column.

Rectifying section and stripping section of the feed column each comprise at least one theoretical plate. The height of the feed within the feed column is not critical per se for the process according to the invention. For energetic reasons, it may be advisable to reduce the size of the stripping section of the feed column in favor of the rectifying section. The stripping section of the feed column preferably accounts for from 1 to 50%, especially from 1 to 30%, of the total number of theoretical plates of the feed column.

The part of the draw column disposed above the side draw and the part disposed below the side draw each comprise at least one theoretical plate. The position of the side draw within the draw column is not critical per se for the process according to the invention. For energetic reasons, it may be advisable to reduce the part disposed above the side draw in favor of the part disposed below the side draw. The part of the draw column disposed above the side draw preferably accounts for from 1 to 50%, especially from 1 to 30%, of the total number of theoretical plates of the draw column.

Although the feed and the side draw can be arranged at the same height, it is generally preferred to mount the feed and the side draw at different heights.

In preferred embodiments, $$Q_{feed} > Q_{draw}$$

in which $Q_{feed}$ is the ratio of the number of theoretical plates of the rectifying section of the feed column to the number of theoretical plates of the stripping section, and $Q_{draw}$ is the ratio of the number of theoretical plates of the part of the draw column disposed above the side draw to the number of theoretical plates of the part disposed below the side draw. Preferably, $Q_{feed} > 4 Q_{draw}$.

In other words, in a dividing wall designed symmetrically with respect to the dividing wall, the feed is preferably lower than the side draw.

The ratio of the total number of theoretical plates of the feed column to the total number of theoretical plates of the draw column is preferably from 0.8 to 1.2.

The vapor stream from the lower combining column is divided between the feed column and the draw column according to the particular pressure drop. It is possible to establish a particular division ratio, for example, by varying the relative cross section of the feed column and draw column. The ratio of the cross-sectional area of the feed column to the cross-sectional area of the draw column is, in the process according to the invention, preferably from 0.25 to 4.

The condensate stream from the upper combining column is divided between the feed column and the draw column preferably in a ratio of from 50:1 to 1:50, preferably in a ratio of from 20:1 to 1:20, especially in a ratio from 10:1 to 1:10.

The inventive distillation is effected preferably at a pressure in the range from 1 to 300 mbar (absolute), preferably from 10 to 300 mbar (absolute), especially from 10 to 100 mbar (absolute).

The crude MA solution is preferably introduced into the feed column in liquid form at a temperature of from 80 to 150° C.

To withdraw or divide condensate at a point in a column, for example to divide the condensate from the upper combining column between the feed column and draw column or to withdraw liquid side draws, collecting trays are appropriately provided.

The preparation of MA by gas phase oxidation of a hydrocarbon is known per se. In general, tube bundle reactors are used. Alternatively, fluidized bed reactors may be used.

The hydrocarbons are generally aliphatic or aromatic, saturated or unsaturated hydrocarbons having at least four carbon atoms, for example 1,3-butadiene, 1-butene, 2-cis-butene, 2-trans-butene, n-butane, $C_4$ mixtures, 1,3-pentadiene, 1,4-pentadiene, 1-pentene, 2-cis-pentene, 2-trans-pentene, n-pentane, cyclopentadiene, dicyclopentadiene, cyclopentene, cyclopentane, $C_5$ mixtures, hexenes, hexanes, cyclohexane and benzene. Preference is given to using 1-butene, 2-cis-butene, 2-trans-butene, n-butane, benzene or mixtures thereof. Particular preference is given to the use of n-butane and n-butane-containing gases and liquids. The n-butane used may, for example, stem from natural gas, from steamcrackers or FCC crackers.

The hydrocarbon is added generally under quantitative control, i.e. while constantly maintaining a defined amount per unit time. The hydrocarbon can be metered in in liquid or gaseous form. Preference is given to metered addition in liquid form with subsequent evaporation before entry into the reactor.

The oxidizing agents used are oxygen-comprising gases, for example air, synthetic air, a gas enriched with oxygen or else pure oxygen, i.e. oxygen stemming from air fractionation. The oxygen-comprising gas is preferably also added under quantitative control.

The gas to be passed through the reactor generally comprises a hydrocarbon concentration of from 0.5 to 15% by volume and an oxygen concentration of from 8 to 25% by volume. The proportion missing from one hundred percent by volume is composed of further gases, for example nitrogen, noble gases, carbon monoxide. carbon dioxide, steam, oxygenated hydrocarbons (e.g. methanol, formaldehyde, formic acid, ethanol, acetaldehyde, acetic acid, propanol, propionaldehyde, propionic acid, acrolein, crotonaldehyde) and mixtures thereof.

In general, vanadium-, phosphorus- and oxygen-containing catalysts (so-called VPO catalysts) are used (see Ullmann's Encyclopedia of Industrial Chemistry, 6th edition, 2000 electronic release, Chapter "MALEIC AND FUMARIC ACIDS, Maleic Anhydride-Production"). These are generally prepared as follows: (1) Synthesis of a vanadyl hydrogenphosphate hemihydrate precursor ($VOHPO_4$ ½ $H_2O$) from a pentavalent vanadium compound (e.g. $V_2O_5$), a penta- or trivalent phosphorus compound (e.g. ortho- and/or pyrophosphoric acid, phosphoric esters or phosphorous acid) and a reducing alcohol (e.g. isobutanol), isolation of the precipitate and drying, if appropriate shaping (e.g. tableting); and (2) preforming to give vanadyl pyrophosphate ($(VO)_2P_2O_7$) by calcination. Suitable catalysts and their preparation are described, for example, in WO 03/078,059, WO 03/078,058, WO 03/078,057 and WO 03/078,310.

To ensure a long catalyst lifetime and further increase in conversion, selectivity, yield, catalyst loading and space-time yield, a volatile phosphorus compound is preferably added to the gas.

At the start, i.e. at the reactor inlet, its concentration is at least 0.2 ppm by volume, i.e. 0.2-10-6 parts by volume of the volatile phosphorus compounds based on the total volume of the gas at the reactor inlet. Preference is given to a content of from 0.2 to 20 ppm by volume, more preferably of from 0.5 to 10 ppm by volume.

Suitable volatile phosphorus compounds include, for example, phosphines and phosphoric esters. Particular preference is given to the $C_1$-$C_4$-alkyl phosphates, very particular preference to trimethyl phosphate, triethyl phosphate and tripropyl phosphate, especially triethyl phosphate.

The gas phase oxidation is performed generally at a temperature of from 350 to 480° C. It can be practised at a pressure below standard pressure (for example up to 0.05 MPa absolute) or below standard pressure (e.g. up to 10 MPa abs). Preference is given to a pressure of from 0.1 to 1.0 MPa absolute, more preferably from 0.1 to 0.5 MPa absolute.

The reaction gas leaving the reactor is cooled in a suitable manner, for example by means of an indirect gas-gas heat exchanger, in which case the heat removed is used to preheat the input gas. The reaction gas can be cooled further, in which case, for example, steam can be raised.

The cooled reaction gas is passed into an absorber in which it is contacted with the high-boiling absorbent. The absorption zone of the absorber appropriately comprises internals, for example random packings such as saddles or rings, for promoting gas-liquid contact. Alternatively, the absorber may comprise a tray column in which the gas-liquid contact proceeds on the trays.

The cooled reaction gas is appropriately introduced into the absorber in a lower region of the absorber, while the absorbent is introduced in an upper region of the absorber, so that the absorbent is conducted in countercurrent to the reaction gas. The MA and some of the oxidation by-products are absorbed into the absorbent, while the other portion of the oxidation by-products and inert gases leave the absorber as offgas. Suitable absorbers are described, for example, in EP-A 612714 and WO 96/29323.

The absorbent should have a high dissolution capacity for MA, a low vapor pressure and sufficient thermal stability. Suitable absorbents are dimethylbenzophenone, dichlorodiphenyl oxide, dialkyl phthalates and dialkyl hexahydrophthalates. Preference is given to di($C_1$-$C_8$-alkyl) phthalates and hexahydrophthalates. These include dimethyl phthalate, diethyl phthalate, dipropyl phthalate, diisopropyl phthalate, dibutyl phthalate diisobutyl phthalate, dimethyl hexahydrophthalate, diethyl hexahydrophthalate, dipropyl hexahydrophthalate, diisopropyl hexahydrophthalate, dibutyl hexahydrophthalate, diisobutyl hexahydrophthalate. Dibutyl phthalate is the most preferred.

BRIEF DESCRIPTION OF THE DRAWING

The process according to the invention is illustrated in detail by the appended FIGURE and the example which follows.

FIG. 1 shows a dividing wall column suitable for performing the process according to the invention.

DETAILED DESCRIPTION OF THE DRAWING

According to FIG. 1, the dividing wall column 1,2,3 comprises a feed column 2A and a draw column 2B, which are separated from one another by a dividing wall and which open at the top into the upper combining column 3 and at the bottom into the lower combining column 1. Above and below the dividing wall region are provided collecting trays with collectors and distributors, which ensure uniform trickle-down through the column. The crude MA solution is introduced continuously into the feed column 2A via the feed 10.

The feed column 2A comprises a rectifying section disposed above the feed point 10 and a stripping section disposed below the feed point 10. The draw column 2B comprises a rectifying section disposed above the side draw 11 and a stripping section disposed below the side draw 11. The pure MA is drawn off via the side draw 11. At the top of the column, the vapors are fed to a condenser 4; the condensate is recycled completely or partly into the upper region of the column 1,2,3; the remainder is discharged in gaseous or liquid form as the low boiler fraction via the line 13. Bottom product is withdrawn from the bottom of the column and recycled partly via the heater into the lower region of the column 1,2,3; the remainder is discharged as higher boiler fraction via the line 12.

EXAMPLE

A dividing wall column with an internal diameter of 64 mm and a total construction height of about 3.5 m was used. The dividing wall extended at a height from about 0.6 to 2 m. The separating internals used were A3-750 structured packing elements from Montz (Hilden). It was thus possible to realize 5 theoretical plates in each case in the region below and above the dividing wall. In the dividing wall region itself, about 12 theoretical plates were installed in each case on the feed side and draw side.

The feed stream into the dividing wall region was about 10 cm above the lower end of the dividing wall. The liquid side draw was mounted on the opposite side of the dividing wall, and about 10 cm from the upper end of the dividing wall.

The column was operated at top pressure 30 mbar (absolute). The bottom temperature at the end of the evaporator was controlled to 200° C. At the top of the column, a temperature of about 93° C. was established. The dividing ratio of the liquid above the dividing wall was adjusted to 1:1. The minimum trickle density over the column was about 1 m$^3$/m$^2$h.

The feed stream comprised dibutyl phthalate as the high-boiling absorbent, MA dissolved therein and further components, for example acetic acid, acrylic acid, maleic acid. The detailed composition is reported in table 1 in the "feed" column (composition determined by gas chromatography).

The feed rate into the column was 1400 g/h. The bottom temperature was kept constant via the side draw rate. On average, the draw rate was 86 g/h. The column was operated stably in this configuration for several days. Within this time, both run samples and collected samples were taken at the bottom and side draw.

By way of example, table 1 shows the results for a "run sample" and a "collected sample". The collected sample was collected continuously and assessed over a period of 16 hours.

TABLE 1

| [%] | Feed | Sidestream run sample | Sidestream collected sample |
| --- | --- | --- | --- |
| Acetic acid | 0.038 | n.d. | n.d. |
| Acrylic acid | 0.096 | n.d. | n.d. |
| Maleic anhydride | 6.271 | 99.8844 | 99.9162 |
| Citraconic anhydride | 0.024 | n.d. | n.d. |
| Benzoic acid | 0.002 | n.d. | 0.0001 |
| Dimeric acrylic acid | 0.000 | 0.0011 | n.d. |
| Maleic acid | 0.252 | 0.0310 | 0.0070 |
| Fumaric acid | 0.004 | 0.0005 | 0.0006 |
| Citraconic acid | 0.047 | 0.0001 | n.d. |
| Monobutyl maleate | 0.017 | 0.0174 | 0.0185 |
| Monobutyl fumarate | 0.002 | n.d. | n.d. |
| Phthalic anhydride | 0.293 | 0.0019 | 0.0027 |

TABLE 1-continued

| [%] | Feed | Sidestream run sample | Sidestream collected sample |
| --- | --- | --- | --- |
| Dibutyl maleate | 0.008 | n.d. | n.d. |
| Dibutyl fumarate | 0.002 | n.d. | n.d. |
| Phthalic acid | 0.002 | 0.0011 | 0.0014 |
| Monobutyl phthalate | 0.095 | n.d. | 0.0002 |
| Dibutyl phthalate | 92.144 | 0.0620 | 0.0528 |
| Unknown | 0.701 | 0.0620 | 0.0528 |
| Color number (APHA) |  | 18 | 15 |
| Water (%) | 0.05 | n.d. | n.d. | n.d. = not detectable

In both cases, the MA content of the samples is more than 99.8%. The amounts of low-boiling components, such as acetic acid and acrylic acid and water, present in the feed stream are no longer detectable in the sidestream. This has a positive effect on the required acid specification and the color number in the pure product (<20 APHA).

COMPARATIVE EXAMPLE

Simulation calculations and sample experiments for obtaining pure MA in a simple column with liquid side draw (without dividing wall) were performed. Pure MA (having a purity of 99.5% by weight or more) can also be obtained with this arrangement. However, the color number of the resulting product is more than 20 and is significantly higher than in the above example. A low color number is an important quality feature for MA.

The invention claimed is:

1. A process for obtaining maleic anhydride by distillation from a solution of maleic anhydride in a high-boiling absorbent which has been obtained by gas phase oxidation of a hydrocarbon and at least partial absorption of the oxidation products into the absorbent, by
   i) introducing the solution into the side of a feed column with a rectifying section disposed above the feed point and a stripping section disposed below the feed point,
   ii) providing an upper combining column which communicates with the upper end of the rectifying section and a lower combining column which communicates with the lower end of the stripping section,
   iii) providing a draw column which communicates with the upper combining column and the lower combining column,
   iv) drawing maleic anhydride off as a side draw from the draw column, and drawing off compounds having a lower boiling point than maleic anhydride at the top of the upper combining column and the high-boiling absorbent at the bottom of the lower combining column;
   wherein the feed column and the draw column are designed as subchambers which extend over a section of the longitudinal dimension of a column, are open at both sides to a combining space on each side and are separated from one another by a dividing wall.

2. The process according to claim 1, wherein the dividing wall is designed with thermal insulation at least in some regions.

3. The process according to claim 1, wherein the upper combining column, feed column, draw column and lower combining column are designed as thermally coupled columns.

4. The process according to claim 1, wherein the maleic anhydride is withdrawn in liquid form at the side draw.

5. The process according to claim 1, wherein the maleic anhydride drawn off as the side draw has a content of less than 10 ppm of acyrlic acid and less than 10 ppm of acetic acid.

6. The process according to claim 1, wherein the stripping section of the feed column accounts for from 1 to 50% of the total number of theoretical plates of the feed column.

7. The process according to claim 1, wherein the part of the draw column disposed above the side draw accounts for from 1 to 50% of the total number of theoretical plates of the draw column.

8. The process according to claim 1, wherein $$Q_{feed} > Q_{draw}$$

in which $Q_{feed}$ is the ratio of the number of theoretical plates of the rectifying section of the feed column to the number of theoretical plates of the stripping section, and $Q_{draw}$ is the ratio of the number of theoretical plates of the part of the draw column disposed above the side draw to the number of theoretical plates of the part disposed below the side draw.

9. The process according to claim 1, wherein the upper combining column and the lower combining column each independently account for from 1 to 60% of the total number of theoretical plates of upper combining column, feed column, draw column and lower combining column.

10. The process according to claim 1, wherein the ratio of the total number of theoretical plates of the feed column to the total number of theoretical plates of the draw column is from 0.8 to 1.2.

11. The process according to claim 1, wherein the feed column and draw column are provided in their entirety or in some regions with structured packings or random packings.

12. The process according to claim 1, wherein the ratio of the cross-sectional area of the feed column to the cross-sectional area of the draw column is from 0.25 to 4.

13. The process according to claim 1, wherein the condensate stream from the upper combining column is divided between the feed column and the draw column in a ratio of from 50:1 to 1:50.

14. The process according to claim 1, wherein the rectification is performed at a pressure in the range from 1 to 300 mbar (absolute).

15. The process according to claim 1, wherein the high-boiling absorbent is selected from di($C_1$-$C_8$-alkyl) phthalates, di($C_1$-$C_8$-alkyl) hexahydrophthalates and mixtures thereof.

16. The process according to claim 1, wherein the hydrocarbon is selected from n-butane, n-butenes, benzene and mixtures thereof.

17. The process according to claim 2, wherein the maleic anhydride is withdrawn in liquid form at the side draw.

18. The process according to claim 3, wherein the maleic anhydride is withdrawn in liquid form at the side draw.

* * * * *